United States Patent [19]

Bodor

[11] 4,145,441
[45] Mar. 20, 1979

[54] SYMPATHOMIMETIC AMINES EXHIBITING ANTI-HEMORRHOIDAL ACTIVITY

[75] Inventor: Nicholas S. Bodor, Lawrence, Kans.

[73] Assignee: Interx Research Corporation, Lawrence, Kans.

[21] Appl. No.: 848,602

[22] Filed: Nov. 4, 1977

[51] Int. Cl.² .................... A61K 31/12; A61K 31/24; A61K 31/135
[52] U.S. Cl. ................................. 424/309; 424/330; 424/331
[58] Field of Search ........................ 424/331, 330, 309

[56] References Cited

U.S. PATENT DOCUMENTS

| | | | |
|---|---|---|---|
| 3,809,714 | 5/1974 | Hussain et al. | 424/311 |
| 3,825,583 | 7/1974 | Hussain et al. | 424/311 |
| 3,839,584 | 10/1974 | Hussain et al. | 424/311 |
| 3,868,401 | 2/1975 | Hussain et al. | 424/311 |

Primary Examiner—Stanley J. Friedman
Attorney, Agent, or Firm—Bacon & Thomas

[57] ABSTRACT

Compounds having the formula:

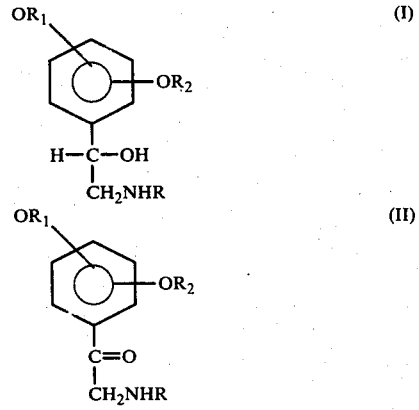

wherein R represents hydrogen or a straight or branched $C_1$-$C_5$ alkyl group; and $R_1$ and $R_2$ which may be the same or different represent an acyl member which is alkanoyl having 1-22 carbon atoms, alkenoyl having one or two double bonds and having 4-22 carbon atoms, cycloalkyl-$C_nH_{2n}$

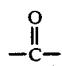

having a total of 4-10 carbon atoms of which 3-7 are ring carbon atoms in cycloalkyl and wherein n is zero, one, or two, phenoxyacetyl, naphthalenecarbonyl, pyridinecarbonyl, phenyl-$C_nH_{2n}$

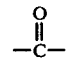

wherein n is zero, one or two and phenyl is unsubstituted or is substituted by 1-3 alkyl having 1-4 carbon atoms, alkoxy having 1-4 carbon atoms, halo, trifluoromethyl, dialkylamino having 2-8 carbon atoms, or alkanoylamino having 1-6 carbon atoms groups;

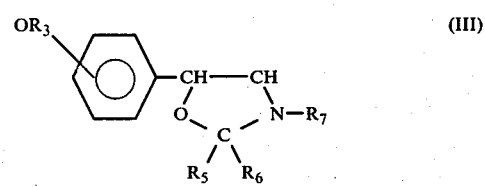

wherein $R_3$ may be hydrogen, hydroxyl or a member defined in accordance with $R_1$ and $R_2$ above or

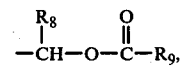

wherein $R_8$ and $R_9$, which may be the same or different represent hydrogen, a $C_1$-$C_8$ open chain or cycloalkyl, a $C_1$-$C_8$ alkoxyalkyl group, a $C_1$-$C_8$ acyloxyalkyl group, a $C_1$-$C_8$ haloalkyl group, a $C_1$-$C_8$ carboxyalkyl group, a $C_2$-$C_8$ alkenylphenyl group, an aryl group, and a substituted aryl group, whose substituents are selected from the group consisting of a halogen atom, an O-lower alkyl ($C_1$-$C_4$) group, an O-acyl group, a nitro group, a carboxyl group, and a carboethoxy group; wherein $R_5$ and $R_6$ which may be the same or different represent hydrogen, $C_1$-$C_{10}$ alkoxyalkyl, $C_1$-$C_{10}$ acyloxyalkyl, phenyl, naphthyl, substituted phenyl or naphthyl, the substituents of which are selected from the group consisting of $C_1$-$C_5$ acyloxy, halogen (Cl, Br, I) or wherein $R_5$ and $R_6$ together with the carbon atom to which they are attached form a cyclopentane or cyclohexane ring or a 5- or 6- membered heterocyclic ring (e.g., piperidine, N-($C_1$-$C_5$)alkylpiperidine, N-acylpiperidine, pyrrolidone, etc.; and wherein $R_7$ represents hydrogen or a ($C_1$-$C_7$) straight or branched alkyl; and the nontoxic pharmaceutically acceptable acid addition salts thereof are disclosed.

Upon rectal application to a warm-blooded animal, e.g., human, theraeutic anti-hemorrhoidal activity (reduction in hemorrhoidal swelling) is observed.

42 Claims, No Drawings

SYMPATHOMIMETIC AMINES EXHIBITING ANTI-HEMORRHOIDAL ACTIVITY

CROSS-REFERENCE TO RELATED APPLIATIONS

The use of the Compounds of Formulas (I), (II) and (III) hereof as topical anti-inflammatory agents is disclosed in U.S. Patent Application, Ser. No. 752,870, filed Dec. 21, 1976.

BACKGROUND OF THE INVENTION

1. Field of the Invention

The present invention is directed to certain selected compounds having anti-hemorrhoidal activity. More specifically, the present invention is directed to certain selected sympathomimetic amine compounds which quite unexpectedly have been observed to exhibit anti-hemorrhoidal activity when rectally administered to a warm-blooded animal.

2. Description of the Prior Art

U.S. Pat. Nos. 3,809,714, 3,825,583, 3,839,584, 3,868,461, 3,966,749, all in the names of the instant assignee; pending U.S. patent application, Ser. No. 758,355 filed Jan. 10, 1977, also in the name of the instant assignee; and British Pat. No. 1,298,772, all disclose a number of sympathomimetic amine derivatives within the above-described formulas (I), (II) and (III). To the best of applicants' knowledge, the compounds of the prior art have not been used to treat hemorrhoidal conditions but have only been used in the treatment of nontopical conditions responsive to sympathomimetic amines, e.g., glaucoma, asthma, nasal decongestion, etc.

It has recently been suggested that epinephrine, because of its vasoconstrictor action, might possibly be useful in treating hemorrhoidal conditions. However, this compound is relatively unstable at rectal pH, i.e., about 6.0 but moreover, does not have the capability to effectively reduce swelling. The compounds of the present invention are among other things characterized as stable at rectal pH and slowly "cleavable" to the parent catecholamine, which through vasoconstriction, reduces the swelling associated with hemorrhoids.

SUMMARY OF THE INVENTION

Quite unexpectedly, it has now been found that compounds having the following formula:

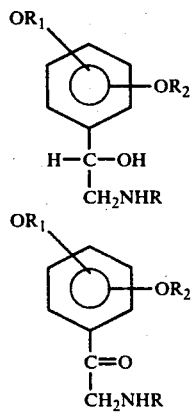

wherein R represents hydrogen or a straight or branched $C_1$-$C_5$ alkyl group; and $R_1$ and $R_2$ which may be the same or different represent an acyl member which is alkanoyl having 1-22 carbon atoms, alkenoyl having one or two double bonds and having 4-22 carbon atoms, cycloalkyl-$C_nH_{2n}$

having a total of 4-10 carbon atoms of which 3-7 are ring carbon atoms in cycloalkyl and wherein n is zero, one, or two, phenoxyacetyl, naphthalenecarbonyl, pyridinecarbonyl, phenyl-$C_nH_{2n}$

wherein n is zero, one or two and phenyl is unsubstituted or is substituted by 1-3 alkyl having 1-4 carbon atoms, alkoxy having 1-4 carbon atoms, halo, trifluoromethyl, dialkylamino having 2-8 carbon atoms, or alkanoylamino having 1-6 carbon atoms groups;

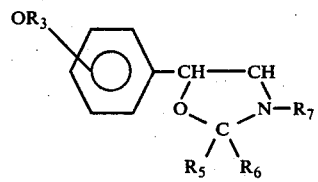

wherein $R_3$ may be hydrogen, hydroxyl or a member defined in accordance with $R_1$ and $R_2$ above or

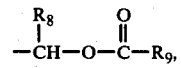

wherein $R_8$ and $R_9$, which may be the same or different represent hydrogen, a $C_1$-$C_8$ open chain or cycloalkyl, a $C_1$-$C_8$ alkoxyalkyl group, a $C_1$-$C_8$ acyloxyalkyl group, a $C_1$-$C_8$ haloalkyl group, $C_1$-$C_8$ carboxylalkyl group, a $C_2$-$C_8$ alkenylphenyl group, an aryl group, and a substituted aryl group, whose substituents are selected from the group consisting of a halogen atom, an O-lower alkyl ($C_1$-$C_4$) group, an O-acyl group, a nitro group, a carboxyl group, and a carboethoxy group; wherein $R_5$ and $R_6$ which may be the same or different represent hydrogen, $C_1$-$C_{10}$ alkoxyalkyl, $C_1$-$C_{10}$ acyloxyalkyl, phenyl, naphthyl, substituted phenyl or naphthyl, the substituents of which are selected from the group consisting of $C_1$-$C_5$ acyloxy, halogen (Cl, Br, I) or wherein $R_5$ and $R_6$ together with the carbon atom to which they are attached form a cyclopentane or cyclohexane ring or a 5- or 6- membered heterocyclic ring (e.g., piperidine, N-$C_1$-$C_5$)alkylpiperidine, N-acylpiperidine, pyrrolidone, etc.; and wherein $R_7$ represents hydrogen or a ($C_1$-$C_7$) straight or branched alkyl; and the nontoxic pharmaceutically acceptable acid addition salts thereof, once thought to only possess sympathomimetic amine activity have now been found useful as rectal anti-hemorrhoidal agents; that is, they reduce hemorrhoidal swelling.

With reference to formulas (I) and (II) above, when substitents "$R_1$" and "$R_2$" in each occurrence represents an acyl member there are included alkanoyl having 1-22 carbon atoms, alkenoyl having one or two double bonds and having 4–22 carbon atoms, cycloalkyl-$C_n$-$H_{2n}$

having a total of 4–10 carbon atoms of which 3–7 are ring carbon atoms in cycloalkyl and wherein n is zero, one, or two, phenoxyacetyl, naphthalenecarbonyl, pyridinecarbonyl, phenyl-$C_nH_{2n}$

wherein n is zero, one or two and phenyl is unsubstituted or is substituted by 1–3 alkyl having 1–4 carbon atoms, alkoxy having 1–4 carbon atoms, halo, trifluoromethyl, dialkylamino having 2–8 carbon atoms, or alkanoylamino having 1–6 carbon atoms groups.

When $R_1$ and $R_2$ in applicants' generic formula is alkanoyl containing 1–22 carbon atoms, there are included both unbranched and branched alkanoyl, for example, formyl, acetyl, propionyl, butyryl, isobutyryl, valeryl, isovaleryl, 2-methylbutanoyl, pivalyl, 3-methylpentanoyl, 3,3-dimethylbutanoyl, 2,2-dimethylpentanoyl, docosanoyl, and 7,7-dimethyloctanoyl. The branched alkanoyl groups are preferred over the unbranched alkanoyl groups.

When $R_1$ and $R_2$ in applicants' generic formula is alkenoyl having one or two double bonds and having 4–22 carbon atoms, there are included, for example, crotonyl, 9-octadecenoyl, 2,5-hexadienoyl, 3,6-octadienoyl, 10,13-octadecadienoyl, and 5,13-docosadienoyl.

When $R_1$ and $R_2$ in applicants' generic formula is cycloalkyl$C_nH_{2n}$

there are included for example the cycloalkanecarbonyl and cycloalkanealkanoyl groups: cyclopropanecarbonyl, 1-methylcyclopropanecarbonyl, cyclopropaneacetyl, alpha-methylcyclopropaneacetyl, 1-methylcyclopropaneacetyl, 2-amylcyclopropaneacetyl, cyclopropanepropionyl, alpha-methylcyclopropanepropionyl, 2-isobutylcyclopropanepropionyl, 2-hexylcyclopropanecarbonyl, cyclobutanepropionyl, 2-methylcyclobutanecarbonyl, 1,3-dimethylcyclobutanecarbonyl, 3,3-dimethylcyclobutanecarbonyl, cyclobutaneacetyl, 2,2-dimethyl-3-ethylcyclobutaneacetyl, cyclobutanepropionyl, cyclopentanecarbonyl, 1-methyl-3-isopropyl, cyclopentanecarbonyl, cyclopentanepropionyl, cyclohexanecarbonyl, cyclohexaneacetyl, 4-methylcyclohexaneacetyl, cycloheptanecarbonyl, 4-methylcycloheptaneacetyl, and cycloheptanepropionyl.

When $R_1$ and $R_2$ in applicants' generic formula is (phenyl or substituted phenyl)-$C_nH_{2n}$

there are included for example benzoyl, phenylacetyl, alpha-phenylpropionyl, beta-phenylpropionyl, p-toluyl, m-toluyl, o-toluyl, o-ethylbenzoyl, p-tert-butylbenzoyl, 3,4-dimethylbenzoyl, 2-methyl-4-ethylbenzoyl, 2,4,6-trimethylbenzoyl, m-methylphenylacetyl, p-isobutylphenylacetyl, beta-(p-ethylphenyl)-propionyl, p-anisoyl, m-anisoyl, o-anisoyl, m-isopropxybenzoyl, p-n-butoxybenzoyl, 3-methoxy-4-ethoxybenzoyl, 3,4,5-trimethoxybenzoyl, 2,4,6-triethoxybenzoyl, p-methoxyphenylacetyl, m-isobutoxyphenylacetyl, 3,4-diethoxyphenylacetyl, beta-(3,4,5-trimethoxyphenyl)propionyl, o-iodobenzoyl, m-bromobenzoyl, p-chlorobenzoyl, p-fluorobenzoyl, 2-bromo-4-chlorobenzoyl, 2,4,6-trichlorobenzoyl, p-chlorophenylacetyl, alpha-(m-bromophenyl)propionyl, p-trifluoromethylbenzoyl, 2,4-di(trifluoromethyl)benzoyl, m-trifluoromethylphenylacetyl, beta-(p-trifluoromethylphenyl)propionyl, 2-methyl-4-methoxybenzoyl, 3-chloro-4-ethoxybenzoyl, beta-(3-methyl-4-chlorophenyl)propionyl, p-dimethylaminobenzoyl, m-diethylaminobenzoyl, p-dibutylaminobenzoyl, p-(N-methyl-N-ethylamino)-benzoyl, o-acetamidobenzoyl, m-propionamidobenzoyl, p-hexanoylaminobenzoyl, 3-chloro-4-acetamidophenylacetyl, and p-acetamidophenylpropionyl.

When $R_1$ and $R_2$ in applicants' generic formula is naphthalenecarbonyl, there are included 1-naphthalenecarbonyl and 2-naphthalenecarbonyl.

When $R_1$ and $R_2$ in applicants' generic formula is pyridinecarbonyl, there are included picolinoyl (2-pyridinecarbonyl)-nicotinoyl(3-pyridinecarbonyl), and isonicotinoyl-(4-pyridinecarbonyl).

Reference to the expressions $C_1$–$C_8$ open chain or cycloalkyl, $C_1$–$C_8$ alkoxyalkyl, $C_1$–$C_8$ acyloxyalkyl, $C_1$–$C_8$ haloalkyl, $C_1$–$C_8$ carboxyalkyl, $C_1$–$C_{10}$ alkoxyalkyl and $C_1$–$C_{10}$ acyloxyalkyl denote (1) a straight or branched alkyl function and (2) the carbon range for the alkyl moiety. Reference to $C_1$–$C_5$ acyloxy denotes a straight or branched acyloxy function derived from a carboxylic acid. Reference to "aryl" denotes phenyl or naphthyl.

Finally, the term "nontoxic pharmaceutically acceptable acid addition salt" as used herein generally includes the nontoxic acid addition salts of selected compounds of formulas (I) and (II), formed with nontoxic inorganic or organic acids. For example, the salts include those derived from inorganic acids such as hydrochloric, hydrobromic, sulfuric, sulfamic, phosphoric, nitric and the like; and the salts prepared from organic acids such as acetic, propionic, succinic, glycollic, stearic, lactic, malic, tartaric, citric, ascorbic, pamoic, maleic, hydroxymaleic, phenylacetic, glutamic, benzoic, salicylic, sulfanilic, fumaric, sulfonic, toluenesulfonic, and the like.

By selecting the appropriate reactants for the ultimate specie desired, the compounds of the present application are conveniently prepared in accordance with the synthetic schemes outlined in the earlier identified references, the entire subject matter of which is incorporated herein by reference.

The compounds of formulas (I) and (II) can be formulated with a wide variety of nontoxic rectally acceptable ointment or suppositories. See, *REMINGTON'S PHARMACEUTICAL SCIENCES* (14th Ed.) 1970.

As for the rectal dose administered, whether a single dose or a daily dose, it will, of course, vary with the needs of the recipient. Accordingly, the rectal dosage administered is not subject to definite bounds, but will usually be a safe but effective anti-hemorrhoidal amount, or the equivalent on a molar basis of the pharmacologically active sympathomimetic amine form produced upon the metabolic release of the active drug to achieve its desired pharmacological and/or physiological effect. Normally, it is found that rectal application of any compound of the present invention in a concentration of about 0.1% to about 10.0% will suffice for anti-hemorrhoidal purposes.

At this juncture, it should be noted that while all compounds within formulas (I), (II) and (III) suffice for applicants' purposes, nevertheless, certain compounds as set out below are preferred:

(1) 3,4-dipivalyloxy-α-[(methylamino)methyl]benzyl alcohol.
(2) 3,4-dipivalyloxy-α-[(isopropylamino)methyl]benzyl alcohol.
(3) 3-pivalyloxy-α-[(methylamino)methyl]benzyl alcohol.
(4) 3,4-dipivalyloxy-α-[(amino)methyl]benzyl alcohol.
(5) 3,4-dihydroxy-α-adrenalone.
(6) 3,4-dipivalyl-α-adrenalone.
(7) 3-(trimethylaceloxy)-α-[(methylamino)methyl]benzyl alcohol.
(8) 3,4-di(3-methyl)-pentanoyloxy-α-[(methylamino)-methyl]-benzyl alcohol.
(9) 3,4-di(3-methyl)-pentanoyloxy-α-[(isopropylamino)methyl]-benzyl alcohol.
(10) 3,4-di(3-methyl)-pentanoyloxy-α-[(t-butylamino)methyl]-benzyl alcohol.
(11) 3,4-di-p-toluyloxy-α-[(methylamino)methyl]benzyl alcohol.
(12) 3,4-di-p-toluyloxy-α-[(isopropylamino)methyl]-benzyl alcohol.
(13) 3,4-di-p-tolulyloxy-α-[(t-butylamino)methyl]benzyl alcohol.
(14) 3,4-dicyclopentyl carbonyloxy-α-[(methylamino)methyl]-benzyl alcohol.
(15) 3,4-dicyclopentyl carbonyloxy-α-[(isopropylamino)-methyl]benzyl alcohol.
(16) 3,4-dicyclopentylcarbonyloxy-α-[(t-butylamino)methyl]-benzyl alcohol.
(17) 3,4-di-2,5-hexadienoyloxy-α-[(methylamino)methyl]-benzyl alcohol.
(18) 3,4-di-2,5-hexadienoyloxy-α-[(isopropylamino)-methyl]-benzyl alcohol.
(19) 3,4-di-2,5-hexadienoyloxy-α-[(t-butylamino)methyl]-benzyl alcohol.
(20) 3,4-diphenylacetyloxy-α-[(methylamino)methyl]-benzyl alcohol.
(21) 3,4-diphenylacetyloxy-α-[(isopropylamino)methyl]-benzyl alcohol.
(22) 3,4-diphenylacetyloxy-α-[(t-butylamino)methyl]benzyl alcohol.
(23) 3,4-dihexanoyloxy-α-(aminomethyl)benzyl alcohol.
(24) 3,4-dipivalyloxy-α-(aminomethyl)benzyl alcohol.
(25) 3,4-di-p-toluyloxy-α-(aminomethyl)benzyl alcohol.
(26) 3,4-di(3,4,5-trimethoxybenzoyl)oxy-α-[(methylamino)-methyl]benzyl alcohol.
(27) 3,4-di(3,4,5-trimethoxybenzoyl)oxy-α-[(isopropylamino)-methyl]benzyl alcohol.
(28) 3,4-di(3,4,5-trimethoxybenzoyl)oxy-α-[(t-butylamino)-methyl]benzyl alcohol.
(29) 3,4-di(p-dimethylaminobenzoyl)oxy-α-[(methylamino)-methyl]benzyl alcohol.
(30) 3,4-di(p-dimethylaminobenzoyl)oxy-α-[(isopropylamino)-methyl]benzyl alcohol.
(31) 3,4-di)p-dimethylaminobenzoyl)oxy-α-[(t-butylamino)-methyl]benzyl alcohol.
(32) 3,4-di(2-naphtolenecarbonyl)oxy-α-[(methylamino)-methyl]benzyl alcohol.
(33) 3,4-di(2-naphtolenecarbonyl)oxy-α-[(isopropylamino)-methyl]benzyl alcohol.
(34) 3,4-di(2-naphtolenecarbonyl)oxy-α-[(t-butylamino)-methyl]benzyl alcohol.
(35) 3-hexanoyloxy-α-[(methylamino)methyl]benzyl alcohol.
(36) 3(p-toluyloxy)-α-[(methylamino)methyl]benzyl alcohol.
(37) 3-phenylacetyloxy-α-[(methylamino)methyl]-benzyl alcohol.
(38) 3-(p-dimethylaminobenzoyl)oxy-α-[(methylamino)methyl]-benzyl alcohol.
(39) 3-(3,4,5-trimethoxybenzoyl)oxy-α-[(methylamino)methyl]-benzyl alcohol.
(40) 3-pivalyloxymethyloxy-α-[(methylamino)methyl]benzyl alcohol.

Without further elaboration, it is believed that one of ordinary skill in the art can, using the preceeding description, utilize the instant invention to its fullest extent. Thus, the following preferred specific embodiments are, therefore, to be construed as merely illustrative and not limitative of the remainder of the specification and claims in any way whatsoever.

EXAMPLE I

THERMAL CHALLENGE ANTI-HEMORRHOIDAL ACTIVITY STUDY

The ability of the compounds of formulas (I), (II) and (III) to effectively reduce swelling is demonstrated by the following test:

The right ear of a rat is placed between two metal cylinders held together by a fource of 2 lbs. The cylinder is heated to 51.6° C. by circulating water from a constant temperature bath. The ear is burned for 10 seconds and then treated one minute later with 50 μl of drug at a concentration of 0.003 M dissolved in isopropyl myristate. Five hours after the burn, the animals are sacrificed and the ears are removed using anatomical guidelines. The % increase in weight of the right ear over the left ear is determined. The anti-hemorrhoidal activity of the tested compounds is determined by their ability to reduce the increase in ear weight,

| Drug | Percent Increase In Ear Weight (Mean of 5 animals) |
|---|---|
| No Drug - No Vehicle | 21.0 |
| Isopropyl myristate | 21.0 |
| Epinephrine . HCl[1] (Prior art compound) | 17.8 |
| DPE . HCl[2] | 4.9 |
| DPE[3] | 5.6 |
| PPE . HCl[4] | 10.6 |
| PPE[5] | 13.9 |
| CPPE[6] | 11.8 |
| DPI . HCl[7] | 10.1 |
| DPNE . HCl[8] | 11.4 |
| DPA . HCl[9] | 10.7 |

[1] 3,4-dihydroxy-α-[(methylamino)methyl]benzyl alcohol HCl
[2] 3,4-dipivalyl-α-[(methylamino)methyl]benzyl alcohol HCl
[3] 3,4-dipivalyl-α-[(methylamino)methyl]benzyl alcohol
[4] 3-hydroxy-α-[(methylamino)methyl]benzyl alcohol HCl
[5] 3-pivalyl-α-[(methylamino)methyl]benzyl alcohol
[6] m-(trimethylacetoxy)-α-[(methylamino)methyl]benzyl alcohol
[7] 3,4-dipivalyl-α-[(isopropylamino)methyl]benzyl alcohol HCl
[8] 3,4-dipivalyl-α-[(amino)methyl]benzyl alcohol HCl
[9] 3,4-dipivalyl-α-adrenalone HCl When the remaining compounds for formulas (I), (II) and (III) of the instant invention are introduced into the above-described study, substantially similar results are obtained.

From the foregoing description, one of ordinary skill in the art can easily ascertain the essential characteristics of this invention, and without departing from the spirit and scope thereof, can make various changes and/or modifications thereto to adapt said invention to various usages and conditions, equitably and intended to be, within the full range of equivalents of the following claims.

What I claim is:

1. A method for reducing hemorrhoidal swelling in a warm-blooded animal which comprises rectally administering thereto, a safe but effective anti-hemorrhoidal amount of a compound having the formula:

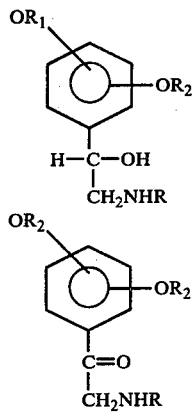

wherein R represents hydrogen or a straight or branched $C_1$–$C_5$ alkyl group; and $R_1$ and $R_2$ which may be the same or different an acyl member which is alkanoyl having 1–22 carbon atoms, alkenoyl having one or two double bonds and having 4–22 carbon atoms, cycloalkyl-$C_nH_{2n}$

having a total of 4–10 carbon atoms of which 3–7 are carbon atoms in cycloalkyl and wherein n is zero, one, or two, phenoxyacetyl, naphthalenecarbonyl, phenyl-$C_nH_{2n}$

wherein n is zero, one or two and phenyl is unsubstituted or is substituted by 1–3 alkyl having 1–4 carbon atoms, alkoxy having 1–4 carbon atoms, halo, trifluoromethyl, dialkylamino having 2–8 carbon atoms, or alkanoylamino having 1–6 carbon atoms groups; and the nontoxic pharmaceutically acceptable acid addition salts thereof.

2. The method of claim 1, wherein said compound is: 3,4-dipivalyloxy-α-[(methylamino)methyl]benzyl alcohol.

3. The method of claim 1, wherein said compound is: 3,4-dipivalyloxy-α-[(isopropylamino)methyl]benzyl alcohol.

4. The method of claim 1, wherein said compound is: 3-pivalyloxy-α-[(methylamino)methyl]benzyl alcohol.

5. The method of claim 1, wherein said compound is: 3,4-dipivalyloxy-α-[(amino)methyl]benzyl alcohol.

6. The method of claim 1, wherein said compound is: 3,4-dipivalyl-α-adrenalone.

7. The method of claim 1, wherein said compound is: m-(trimethylaceloxy)-α-[(methylamino)methyl]benzyl alcohol.

8. The method of claim 1, wherein said compound is: 3,4-di(3-methyl)-pentanoyloxy-α-[(methylamino)methyl]-benzyl alcohol.

9. The method of claim 1, wherein said compound is: 3,4-di(3-methyl)-pentanoyloxy-α-[(isopropylamino)-methyl]benzyl alcohol.

10. The method of claim 1, wherein said compound is: 3,4-di(3-methyl)-pentanoyloxy-α-[(t-butylamino)methyl]-benzyl alcohol.

11. The method of claim 1, wherein said compound is: 3,4-di-p-toluyloxy-α-[(methylamino)methyl]benzyl alcohol.

12. The method of claim 1, wherein said compound is: 3,4-di-p-toluyloxy-α-[(isopropylamino)methyl]benzyl alcohol.

13. The method of claim 1, wherein said compound is: 3,4-di-p-toluyloxy-α-[(t-butylamino)methyl]benzyl alcohol.

14. The method of claim 1, wherein said compound is: 3,4-dicyclopentyl carbonyloxy-α-[(methylamino)methyl]-benzyl alcohol.

15. The method of claim 1, wherein said compound is: 3,4-dicyclopentyl carbonyloxy-α-[(isopropylamino)-methyl]-benzyl alcohol.

16. The method of claim 1, wherein said compound is: 3,4-dicyclopentyl carbonyloxy-α-[(t-butylamino)methyl]-benzyl alcohol.

17. The method of claim 1, wherein said compound is: 3,4-di-2,5-hexadienoyloxy-α-[(methylamino)methyl]-benzyl alcohol.

18. The method of claim 1, wherein said compound is: 3,4-di-2,5-hexadienoyloxy-α-[(isopropylamino)methyl]-benzyl alcohol.

19. The method of claim 1, wherein said compound is: 3,4-diphenylacetyloxy-α-[(methylamino)methyl]benzyl alcohol.

20. The method of claim 1, wherein said compound is: 3,4-di-2,5-hexadienoyloxy-α-[(t-butylamino)methyl]-benzyl alcohol.

21. The method of claim 1, wherein said compound is: 3,4-diphenylacetyloxy-α-[(isopropylamino)methyl]-benzyl alcohol.

22. The method of claim 1, wherein said compound is: 3,4-diphenylacetyloxy-α-[(t-butylamino)methyl]benzyl alcohol.

23. The method of claim 1, wherein said compound is: 3,4-dihexanoyloxy-α-(aminomethyl)benzyl alcohol.

24. The method of claim 1, wherein said compound is: 3,4-di-p-toluyloxy-α-(aminomethyl)benzyl alcohol.

25. The method of claim 1, wherein said compound is: 3,4-di(3,4,5-trimethoxybenzoyl)oxy-α-[(methylamino)methyl]benzyl alcohol.

26. The method of claim 1, wherein said compound is: 3,4-di(3,4,5-trimethoxybenzoyl)oxy-α-[(isopropylamino)-methyl]benzyl alcohol.

27. The method of claim 1, wherein said compound is: 3,4-di-(3,4,5-trimethoxybenzoyl)oxy-α-[(t-butylamino)-methyl]benzyl alcohol.

28. The method of claim 1, wherein said compound is: 3,4-di(p-dimethylaminobenzoyl)oxy-α-[(methylamino)-methyl]benzyl alcohol.

29. The method of claim 1, wherein said compound is: 3,4-di(p-dimethylaminobenzoyl)oxy-α-[(isopropylamino)-methyl]benzyl alcohol.

30. The method of claim 1, wherein said compound is: 3,4-di(p-dimethylaminobenzoyl)oxy-α-[(t-butylamino)-methyl]benzyl alcohol.

31. The method of claim 1, wherein said compound is: 3,4-di(2-naphtolenecarbonyl)oxy-α-[(methylamino)methyl]benzyl alcohol.

32. The method of claim 1, wherein said compound is: 3,4-di(2-naphtolenecarbonyl)oxy-α-[(isopropylamino)-methyl]benzyl alcohol.

33. The method of claim 1, wherein said compound is: 3,4-di(2-naphtolenecarbonyl)-oxy-α-[(t-butylamino)-methyl]benzyl alcohol.

34. The method of claim 1, wherein said compound is: 3-hexanoyloxy-α-[(methylamino)methyl]benzyl alcohol.

35. The method of claim 1, wherein said compound is: 3-(p-toluyloxy)-α-[(methylamino)methyl]benzyl alcohol.

36. The method of claim 1, wherein said compound is: 3-phenylacetyloxy-α-[(methylamino)methyl]benzyl alcohol.

37. The method of claim 1, wherein said compound is: 3-(p-dimethylaminobenzoyl)oxy-α-[(methylamino)-methyl]-benzyl alcohol.

38. The method of claim 1, wherein said compound is: 3-(3,4,5-trimethoxybenzoyl)oxy-α-[(methylamino)-methyl]-benzyl alcohol.

39. The method of claim 1, wherein said compound is: 3-pivalyloxymethyloxy-α-[(methylamino)methyl]-benzyl alcohol.

40. The method of claim 1, wherein said compound is topically co-administered with a nontoxic pharmaceutically acceptable rectal carrier.

41. The method of claim 40, wherein said carrier is as rectal ointment vehicle.

42. The method of claim 40, wherein said carrier is a suppository vehicle.

* * * * *